United States Patent [19]

Takemoto et al.

[11] Patent Number: 5,616,791
[45] Date of Patent: Apr. 1, 1997

[54] METHOD OF PREPARING L-ASPARTYL-D-α-AMINOALKANE CARBOXYLIC ACID-(S)-N-α-ALKYLBENZYLAMIDE

[75] Inventors: Tadashi Takemoto; Toyoto Hijiya, both of Kawasaki, Japan

[73] Assignee: Ajinomoto Co., Inc., Tokyo, Japan

[21] Appl. No.: 524,812

[22] Filed: Sep. 7, 1995

[30] Foreign Application Priority Data

Sep. 7, 1994 [JP] Japan ................................ 6-213704

[51] Int. Cl.$^6$ ................................................ C07C 229/08
[52] U.S. Cl. .................................................... 562/450
[58] Field of Search ............................................ 562/450

[56] References Cited

U.S. PATENT DOCUMENTS 4,508,180  4/1985  Yamatani et al. ........................ 562/450
4,550,180  10/1985  Takemoto et al. ....................... 549/253
5,286,509  2/1994  D'Angelo et al. ....................... 562/450

FOREIGN PATENT DOCUMENTS 0027319  4/1981  European Pat. Off. .
0529413  3/1993  European Pat. Off. .
WO94/00028  1/1994  WIPO .

OTHER PUBLICATIONS

Chemical Abstracts, vol. 121, No. 11, Sep. 12, 1994, AN–134755a, I.Y. Lee, et al., "Synthesis of an Aspartame Precursor Using Thermolysin in Organic Two–Phase System".

Primary Examiner—Joseph Conrad
Attorney, Agent, or Firm—Oblon, Spivak, McClelland, Maier & Neustadt, P.C.

[57] ABSTRACT

The present invention provides a method of preparing L-aspartyl-D-α-aminoalkane carboxylic acid-(S)-N-α-alkylbenzylamide which is less expensive and more efficient than previous methods using N-protected-L-aspartic anhydride.

14 Claims, No Drawings

METHOD OF PREPARING L-ASPARTYL-D-α-AMINOALKANE CARBOXYLIC ACID-(S)-N-α-ALKYLBENZYLAMIDE

BACKGROUND OF THE INVENTION

1. Field of the Invention

The present invention relates to a method of preparing L-aspartyl-D-α-aminoalkanecarboxylic acid-(S)-N-α-alkylbenzylamide which is a sweetener.

2. Discussion of the Background

Present eating habits have involved an increase intake of sugars compared to past diets, resulting in an increase in obesity and other diseases. To avoid these problems many low-calorie sweeteners have been developed as alternatives to sugar. For example, aspartame, is widely used and has excellent safety and sweetness quality. Unfortunately, aspartame is relatively unstable; therefore, it is desirable to find a sweetener with improved stability.

U.S. Pat. No. 5,286,509 discloses L-aspartyl-D-α-aminoalkanecarboxylic acid-(S)-N-α-alkylbenzylamide which has a higher sweetness and a higher stability than aspartame and is a promising compound as a dietary sweetener. N-benzyloxy-carbonyl-L-aspartic acid β-benzylester in which the amino group and the β-carboxylic group of L-aspartic acid are protected is condensed with D-α-aminoalkanecarboxylic acid-(S)-N-α-alkylbenzylamide using dicyclohexylcarbodiimide, and then the benzyloxycarbonyl and benzyl groups are removed by catalytic hydrogenation to yield the product. However, this method is not suitable for industrial production since it employs two expensive materials, N-benzyloxycarbonyl-L-aspartic acid β-benzylester as a raw material and dicyclo-hexylcarbodiimide as a condensation agent.

U.S. Pat. No. 5,286,509 also describes that N-protected-L-aspartic anhydride such as N-benzyloxy carbonyl-L-aspartic anhydride or N-formyl-L-aspartic anhydride can be alternatively employed, but no specific processes or conditions are disclosed.

SUMMARY OF THE PRESENT INVENTION

Accordingly, one object of the present invention is to provide a method of preparing L-aspartyl-D-α-aminoalkane carboxylic acid-(S)-N-α-alkylbenzylamide which is less expensive and more efficient than previous methods using N-protected-L-aspartic anhydride.

The present inventors have now discovered that L-aspartyl-D-α-aminoalkanecarboxylic acid-(S)-N-α-alkylbenzylamide can be obtained by:

reacting N-protected-L-aspartic anhydride and D-α-aminoalkane carboxylic acid-(S)-N-α-alkylbenzylamide in the presence of acetic acid and an organic solvent which is immiscible with water (i.e., can not be mixed uniformly with water);

without isolating N-protected-L-aspartyl-D-α-aminoalkane-carboxylic acid-(S)-N-α-alkylbenzylamide thus produced, adding an aqueous solvent directly to the reaction mixture to form a diphasic system;

removing the protective group in the diphase system; separating the organic layer; and then crystallizing L-aspartyl-D-α-aminoalkanecarboxylic acid-(S)-N-α-alkylbenzylamide from the aqueous solvent, i.e. the aqueous phase.

While the method of producing the desired dipeptide amide using N-protected-L-aspartic anhydride (the prior art method) comprises three processes, i.e., (1) a process wherein N-protected-dipeptide amide is produced by coupling the anhydride with the amide, (2) a process wherein the protective group is removed and (3) a process wherein the desired free dipeptide amide is separated, the method of this invention makes it possible to perform the above three processes in one reaction device (one pot reaction) because there is no need to separate the intermediate N-protected-dipeptide amide. Thus, this one pot reaction is better from the view point of industrial production then prior art processes.

Reaction of N-protected-L-aspartic anhydride and D-α-aminoalkane carboxylic acid-(S)-N-α-alkylbenzylamide Suitable N-protecting groups for L-aspartic anhydride which can be employed in the present invention include benzyloxycarbonyl, formyl, t-butoxy-carbonyl, trifluoroacetyl, phthalyl, benzylidene and the like. Since benzyloxycarbonyl and formyl groups are available at low cost and can also be removed at low costs, these are preferred industrially.

Suitable organic solvents which can be used in the reaction of N-protected-L-aspartic anhydride and D-α-aminoalkanecarboxylic acid-(S)-N-α-alkylbenzylamide and which are immiscible with water include aromatic hydrocarbons such as toluene and xylene, fatty acid esters such as ethyl acetate and butyl acetate, halogenated hydrocarbons such as methylene chloride and chloroform and ethers such as tetrahydrofuran and dioxane. Toluene and xylene being preferred industrially.

Suitable N-protected-L-aspartic anhydrides which can be used as starting materials in the present invention, except for N-formyl-L-aspartic anhydride, can be readily obtained by treating corresponding N-protected-L-aspartic acid with acetic anhydride as described in U.S. Pat. No. 4,508,912. N-formyl-L-aspartic anhydride can be readily obtained by treating L-aspartic acid and formic acid with acetic anhydride as described in U.S. Pat. 4,550,180.

The other starting material, D-α-aminoalkanecarboxylic acid-(S)-N-α-alkylbenzyl-amide, can be readily obtained by condensing a N-protected-D-α-aminoalkanecarboxylic acid with (S)-α-alkylbenzylamine using a condensation agent such as dicyclohexylcarbodiimide followed by removing the protective group as described in U.S. Pat. No. 5,286,509.

Preferred D-α-aminoalkanecarboxylic acid-(S)-N-α-alkylbenzyl-amides include D-valine-(S)-N-α-ethylbenzylamide or D-α-aminobutyric acid-(S)-N-α-ethyl-benzylamide The reaction of N-protected-L-aspartic anhydride with D-α-aminoalkanecarboxylic acid-(S)-N-α-alkylbenzylamide may, for example, be conducted by adding both reactants to a mixture of acetic acid and an organic solvent. In practice the reaction is carried out as described below since the amide is an oil. D-α-aminoalkanecarboxylic acid-(S)-N-α-alkylbenzylamide is first dissolved in an organic solvent containing acetic acid and to this solution N-protected-L-aspartic anhydride is added. Alternatively, to a solution or slurry of N-protected-L-aspartic anhydride in acetic acid a solution of D-α-aminoalkanecarboxylic acid-(S)-N-α-alkylbenzylamide in an organic solvent is added. Further alternatively, to a solution or slurry of N-protected-L-aspartic anhydride in a mixture of acetic acid and an organic solvent, a solution of D-α-aminoalkanecarboxylic acid-(S)-N-α-alkylbenzylamide in an organic solvent or in an organic solvent containing acetic acid is added.

Although the concentrations of N-protected-L-aspartic anhydride and D-α-aminoalkanecarboxylic acid-(S)-N-α- alkylbenzylamide in the reaction mixture are not specifically limited, they are preferably added in equal molar amounts, preferably in the range of 0.03 to 10.0 mol/l, more preferably in the range of 0.05 to 5.0 mol/l. An excessively diluted solution is undesirable for commercial applications since it yields a large volume of the reactant.

Although N-protected-L-aspartic anhydride and D-α-aminoalkanecarboxylic acid-(S)-N-α-alkylbenzylamide are employed usually in equal molar amounts, the amount of one exceeding the amount of the other causes no problems in the reaction.

The ratio of acetic acid in the mixture of acetic acid and the organic solvent ranges usually from 5 to 95% by volume, preferably from 5 to 40%, more preferably from 15 to 25%.

The reaction temperature is not higher than the boiling point of the solvent, usually −30° to 100° C., preferably 0° to 40° C., more preferably 15°–30° C. The reaction time may vary depending on the reaction temperature and concentrations, and usually ranges from 1 to 10 hours.

Acetic acid which has been used in the reaction can readily be recovered by the procedure described below. Thus, by adding the organic solvent identical to that employed in the reaction and then concentrating it, almost the entire amount of acetic acid is evaporated. Since, through this procedure, the reaction mixture is replaced with the organic solvent, it can be used directly in the subsequent step, while acetic acid can easily be recovered by separating from the mixture with the organic solvent by means of distillation.

Deprotection of N-protected-L-aspartyl-D-α-aminoalkanecarboxylic acid-(S)-N-α-alkylbenzylamide To the reaction mixture thus obtained is added water or water containing a solvent which can be mixed uniformly with water, such as methanol, ethanol, dimethylformamide and dioxane to form a two-layer mixture, and then the protective group is removed. When the protective group is benzyloxycarbonyl group, an aqueous solvent is added and then Pd/C (1 mg or more of Pd per mole of benzyloxycarbonyl group) is added to carry out catalytic hydrogenation. Although the reaction temperature is not particularly limited, the deprotection reaction is usually conducted at a temperature of from 10° C. to 70° C.

The amount of the aqueous solvent to be added is not particularly limited, but an excessively large amount gives an undesirably large volume and accordingly the concentration as N-protected-L-aspartyl-D-α-aminoalkanecarboxylic acid-(S)-N-α-alkylbenzylamide from 0.1 to 10.0 g/dl, preferably 0.05 to 5.0 g/dl, is usually employed.

In case that the protective group which can be removed with an acid, such as formyl, t-butoxycarbonyl and benzylidene groups, the removal of the protective group can be done easily by the addition of an aqueous solvent which an acid concentration is 0.1N or higher (acid in a molar amount in excess of 0.5 times that of the protective group) at room temperature or higher. It is a matter of course that the acid is added after an addition of the aqueous solvent. Although the acid to be used is not particularly limited, hydrochloric acid and sulfuric acid are usually employed since they are readily available at low cost.

The reaction time varies depending on the reaction temperature, and ranges from 1 to 3 days at room temperature, from 1 to 4 hours at 70° C. and from 5 minutes to 1 hour under reflux. In the case of trifluoroacetyl or phthalyl group which can be removed with a base, the base may be employed in a manner similar to that used for the acid as described above.

Crystallization of L-aspartyl-D-α-aminoalkanecarboxylic acid-(S)-N-α-alkylbenzyl amide After completion of the deprotection, the organic layer is allowed to separate from the aqueous phase the pH of the aqueous layer is adjusted between 4.5 and 5.5, and then L-aspartyl-D-α-aminoalkanecarboxylic acid-(S)-N-α-alkylbenzyl amide is crystallized out by cooling to be isolated by filtration. The pH may be adjusted using the acids and bases routinely employed such as hydrochloric acid, sulfuric acid, sodium bicarbonate, sodium carbonate, sodium hydroxide, triethylamine and the like.

Although the temperature of crystallization is not particularly limited, a temperature of 15° C. or lower is preferable in view of the yield. It is also possible to concentrate the mother liquor of the filtration and subsequently cool it to recover L-aspartyl-D-α-aminoalkanecarboxylic acid-(S)-N-α-alkylbenzyl-amide easily.

It is obvious to those skilled in the art that some L-aspartyl-D-α-aminoalkanecarboxylic acid-(S)-N-α-alkylbenzylamide will be produced in the reactions described above, but it can be readily eliminated by the crystallization described above.

Having generally described this invention, a further understanding can be obtained by reference to certain specific examples which are provided herein for purposes of illustration only and are not intended to be limiting unless otherwise specified.

EXAMPLES

Example 1

To a slurry obtained by adding 7.16 g (0.05 moles) of N-formyl-L-aspartic anhydride to 50 ml of acetic acid, 250 ml of toluene containing 11.7 g (0.05 moles) of D-valine-N-(S)-ethyl-benzylamide was added over a period of 30 minutes while stirring at room temperature, and the mixture was then stirred overnight at room temperature. Quantitative analysis using HPLC indicated that 0.031 moles of N-formyl-α-L-aspartyl-D-valine-N-(S)-ethyl-benzylamide (yield of 62.0% based on D-valine-N-(S)-ethyl-benzylamide) were produced in the reaction mixture. 750 ml of 0.5N hydrochloric acid was added to the reaction mixture, which was then stirred while heating for 2 hours at 70° C. The toluene layer was subjected to layer separation to isolate the aqueous layer, which was cooled to room temperature and then adjusted to pH 5 with 1.5% sodium carbonate. After adding water to make the volume 1100 ml, the mixture was allowed to stand in a refrigerator overnight. The crystal precipitated was isolated by filtration and dried to obtain 8.39 g (0.024 moles) of α-L-aspartyl-D-valine-N-(S)-ethyl-benzylamide. Yield: 48.0% based on D-valine-N-(S)-ethyl-benzylamide.

Example 2

To a slurry obtained by adding 7.16 g (0.05 moles) of N-formyl-L-aspartic anhydride to 50 ml of acetic acid, 250 ml of toluene containing 11.0 g (0.05 moles) of D-α-aminobutyric acid-N-(S)-ethylbenzylamide were added over a period of 30 minutes while stirring at room temperature, and the mixture was then stirred overnight at room temperature. Quantitative analysis using HPLC indicated that 0.035 moles of N-formyl-α-L-aspartyl-D-α-aminobutyric acid-N-(S)-ethylbenzylamide (yield of 69.6 % based on D-α-aminobutyric acid-N-(S)-ethylbenzylamide) were produced in the reaction mixture. 350 ml of 1N hydrochloric acid was added to the reaction mixture, which was then stirred while heating for 1.5 hours at 70° C. The toluene layer was subjected to layer separation to isolate the aqueous layer, which was concentrated under reduced pressure to the volume of 250 ml, and at room temperature adjusted to pH 5 with 15% sodium carbonate. After adding water to make the volume 400 ml, the mixture was allowed to stand in a refrigerator overnight. The crystal precipitated was isolated by filtration and dried to obtain 8.39 g (0.024 moles) of α-L-aspartyl-D-aminobutyric acid-N-(S)-ethylbenzylamide. Yield: 54.0% based on D-α-aminobutyric acid-N-(S)-ethyl-benzylamide.

Example 3

To a slurry obtained by adding 7.16 g (0.05 moles) of N-formyl-L-aspartic anhydride to 50 ml of acetic acid, 250 ml of toluene containing 11.7 g (0.05 moles) of D-valine-N-(S)-ethyl-benzylamide was added over a period of 30 minutes while stirring at room temperature, and the mixture was then stirred overnight at room temperature. Quantitative analysis using HPLC indicated that 0.031 moles of N-formyl-α-L-aspartyl-D-valine-N-(S)-ethyl-benzylamide (yield of 62.0 % based on D-valine-N-(S)-ethyl-benzylamide) were produced in the reaction mixture. 750 ml of 1N hydrochloric acid was added to the reaction mixture, which was then stirred while heating for 2 hours at 70° C. The toluene layer was subjected to layer separation to isolate the aqueous layer, which was cooled to room temperature and then adjusted to pH 5 with 15% sodium carbonate. After adding water to make the volume 1100 ml, the mixture was allowed to stand in a refrigerator overnight. The crystal precipitated was isolated by filtration and dried to obtain 8.64 g (0.0247 moles) of α-L-aspartyl-D-valine-N-(S)-ethylbenzylamide. Yield: 49.4% based on D-valine-N-(S)-ethylbenzylamide.

Example 4

To a slurry obtained by adding 12.45 g (0.05 moles) of N-benzyloxycarbonyl-L-aspartic anhydride to the mixture of 20 ml of acetic acid and 30 ml of toluene, 250 ml of toluene containing 11.7 g (0.05 moles) of D-valine-N-(S)-ethylbenzylamide was added over a period of 30 minutes while stirring at room temperature, and the mixture was then stirred for 5 hours at room temperature. Quantitative analysis using HPLC indicated that 0.029 moles of N-benzyloxycarbonyl-α-L-aspartyl-D-valine-N-(S)ethylbenzylamide (yield of 57.6% based on D-valine-N-(S)-ethylbenzylamide) were produced in the reaction mixture. 500 ml of water and 0.2 g of 10% Pd/C were added to the reaction mixture, which was then subjected to catalytic hydrogenation for 2 hours at 50° C. The toluene layer was subjected to layer separation to isolate the aqueous layer, which was adjusted to pH 5 with 15% sodium carbonate. After adding water to make the volume 900 ml, the mixture was allowed to stand in a refrigerator overnight. The crystal precipitated was isolated by filtration and dried to obtain 8.16 g (0.0234 moles) of α-L-aspartyl-D-valine-N-(S)-ethylbenzylamide. Yield: 46.8% based on D-valine-N-(S)-ethylbenzylamide.

Example 5

To a slurry obtained by adding 7.16 g (0.05 moles) of N-formyl-L-aspartic anhydride to 30 ml of acetic acid, 100 ml of toluene containing 11.7 g (0.05 moles) of D-valine-N-(S)-ethyl-benzylamide were added over a period of 90 minutes while stirring at 15° C., and then the mixture was stirred for 3 hours at room temperature. Quantitative analysis using HPLC indicated that 0.030 moles of N-formyl-α-L-aspartyl-D-valine-N-(S)-ethylbenzylamide (yield of 60.0% based on D-valine-N-(S)-ethyl-benzylamide) were produced in the reaction mixture. 500 ml of 0.5N hydrochloric acid was added to the reaction mixture, which was then heated under reflux for 30 minutes. The toluene layer was subjected to layer separation to isolate the aqueous layer, which was cooled to room temperature and then adjusted to pH 5 with 15% sodium carbonate. After adding water to make the volume 1000 ml, the mixture was allowed to stand in a refrigerator overnight. The crystal precipitated was isolated by filtration and dried to obtain 8.56 g (0.0245 moles) of α-L-aspartyl-D-valine-N-(S)-ethyl-benzylamide Yield: 49.0% based on D-valine-N-(S)-ethylbenzyl-amide.

Example 6

To a slurry obtained by adding 12.45 g (0.05 moles) of N-benzyloxycarbonyl-L-aspartic anhydride to the mixture of 20 ml of acetic acid and 30 ml of toluene, 200 ml of toluene containing 11.7 g (0.05 moles) of D-α-aminobutyric acid-N-(S)-ethylbenzylamide was added over a period of 30 minutes while stirring at room temperature, and the mixture was then stirred for 5 hours at room temperature. Quantitative analysis using HPLC indicated that 0.0327 moles of N-benzyloxycarbonyl-α-L-aspartyl-D-α-aminobutyric acid-N-(S)-ethylbenzylamide (yield of 65.3 % based on D-α-aminobutyric acid-N-(S)-ethyl-benzylamide) were produced in the reaction mixture. 300 ml of water and 0.2 g of 10% Pd/C were added to the reaction mixture, which was then subjected to catalytic hydrogenation for 2 hours at 50° C. The toluene layer was subjected to layer separation to isolate the aqueous layer, which was adjusted to pH 5 with 15% sodium carbonate. After adding water to make the volume 350 ml, the mixture was allowed to stand in a refrigerator overnight. The crystal precipitated was isolated by filtration and dried to obtain 8.16 g (0.0234 moles) of α-L-aspartyl-D-α-aminobutyric acid-N-(S)-ethylbenzyla-mide. Yield: 57.6% based on D-α-amino-butyric acid-N-(S)-ethylbenzylamide.

Example 7

13.3 g (0.1 mole) of L-aspartic acid was added to the mixture of 6.0 g of formic acid and 20.6 g of acetic anhydride, and the mixture was stirred for 4 hours at 50° C. After cooling the reaction mixture to 20° C., the crystal of N-formyl-L-aspartic anhydride precipitated was isolated by filtration, and washed with 30 ml of ethylether. After drying, 10.8 g (0.075 moles) of N-formyl-L-aspartic anhydride were obtained. The crystal thus obtained was admixed with 75 ml of acetic acid to form a slurry, to which 700 ml of toluene containing 16.4 g (0.07 moles) of D-valine-N-(S)-ethylbenzylamide was added over a period of 40 minutes while stirring at 15° C., and the mixture was stirred for further 1 hour at 60° C. Quantitative analysis using HPLC indicated that 0.044 moles of N-formyl-α-L-aspartyl-D-valine-N-(S)-ethylbenzylamide (yield of 62.9% based on D-valine-N-(S)-ethylbenzylamide) were produced in the reaction mixture. 1000 ml of 0.5N hydrochloric acid was added to the reaction mixture, which was then heated under reflux for 20 minutes. The toluene layer was subjected to layer separation to isolate the aqueous layer, which was cooled to 40° C. and then adjusted to pH 5 with 15% sodium carbonate. After stirring for 5 hours at 10° C., the crystal precipitated was isolated by filtration and dried to obtain 11.65 g (0.0333 moles) of α-L-aspartyl-D-valine-N-(S)-ethylbenzylamide. Yield: 47.6% based on D-valine-N-(S)-ethylbenzylamide.

Having now fully described the invention, it will be apparent to one of ordinary skill in the art that many changes and modifications can be made thereto without departing from the spirit or scope of the invention as set forth herein.

This application is based on Japanese Patent Application No. 213704/1994, filed in the Japanese Patent Office on Sep. 7, 1994, the entire contents of which is incorporated herein by reference.

What is claimed as new and is desired to be secured by Letters Patent of the United States is:

1. A method of preparing L-aspartyl-D-α-amino-alkanecarboxylic acid-(S)-N-α-alkylbenzylamide comprising the sequential steps of:

reacting N-protected-L-aspartic anhydride and D-α-aminoalkanecarboxylic acid-(S)-N-α-alkylbenzylamide in the presence of acetic acid in an organic solvent which can not be mixed uniformly with water, adding an aqueous solvent thereto, removing the protective group in a diphase system, separating the organic layer, and crystallizing L-aspartyl-D-α-aminoalkanecarboxylic acid-(S)-N-α-alkylbenzylamide in the aqueous phase.

2. The method according to claim 1, wherein the protective group for N-protected-L-aspartic anhydride is a benzyloxycarbonyl, formyl, t-butoxycarbonyl, trifluoroacetyl, phthalyl or benzylidene group.

3. The method of claim 2, wherein said protective group is a benzyloxycarbonyl or formyl group.

4. The method according to claim 2, wherein said protective group is formyl and is removed by hydrolyzing with HCl.

5. The method of claim 1, wherein said organic solvent is an aromatic hydrocarbon, a fatty acid ester, a halogenated hydrocarbon or an ether.

6. The method according to claim 5, wherein said organic solvent is toluene.

7. The method according to claim 1, wherein D-α-aminoalkane-carboxylic acid-(S)-N-α-alkylbenzylamide is D-valine-(S)-N-α-ethylbenzylamide or D-α-aminobutyric acid-(S)-N-α-ethyl-benzylamide.

8. The method according to claim 1, wherein the concentrations of N-protected-L-aspartic anhydride and D-α-aminoalkanecarboxylic acid-(S)-N-α-alkyl-benzylamide in the reaction mixture are in the range of 0.03 to 10.0 mol/l.

9. The method according to claim 8, wherein the concentrations of N-protected-L-aspartic anhydride and D-α-aminoalkanecarboxylic acid-(S)-N-α-alkyl-benzylamide in the reaction mixture are in the range of 0.05 to 5.0 mol/l.

10. The method according to claim 1, wherein the ratio of acetic acid in the mixture of acetic acid and the organic solvent ranges from 5 to 95% by volume, based on the total volume of solvent.

11. The method according to claim 10, wherein the ratio of acetic acid in the mixture of acetic acid and the organic solvent ranges from 5 to 40%.

12. The method according to claim 11, wherein the ratio of acetic acid in the mixture of acetic acid and the organic solvent ranges from 15 to 25%.

13. The method of claim 1, wherein the amount of aqueous solvent is from 0.1 to 10.0 g/dl.

14. The method of claim 13, wherein the amount of aqueous solvent is from 0.05 to 5.0 g/dl.

* * * * *